(12) United States Patent
Ismail et al.

(10) Patent No.: US 9,545,781 B2
(45) Date of Patent: Jan. 17, 2017

(54) CHLORINE ANALYTICAL TEST ELEMENT AND A STABILIZED N, N-DIETHYL-P-PHENYLENEDIAMINE SOLUTION

(71) Applicant: HACH COMPANY, Loveland, CO (US)

(72) Inventors: Ibrahim A. Ismail, Osceola, IN (US); Matthew Hertel, Granger, IN (US); Teresa Lynn Swanson, Elkhart, IN (US)

(73) Assignee: Hach Company, Loveland, CO (US)

( * ) Notice: Subject to any disclaimer, the term of this patent is extended or adjusted under 35 U.S.C. 154(b) by 13 days.

(21) Appl. No.: 14/310,512

(22) Filed: Jun. 20, 2014

(65) Prior Publication Data

US 2015/0050195 A1    Feb. 19, 2015

Related U.S. Application Data

(60) Provisional application No. 61/866,738, filed on Aug. 16, 2013.

(51) Int. Cl.
*B32B 38/00* (2006.01)
*G01N 31/22* (2006.01)

(52) U.S. Cl.
CPC ............ *B32B 38/164* (2013.01); *G01N 31/224* (2013.01); *Y10T 436/193333* (2015.01)

(58) Field of Classification Search
CPC ................. B32B 38/164; G01N 31/224; Y10T 436/193333
See application file for complete search history.

(56) References Cited

U.S. PATENT DOCUMENTS

| | | | |
|---|---|---|---|
| 3,937,613 A | 2/1976 | Rosicky | |
| 4,071,321 A | 1/1978 | Lam | |
| 4,275,031 A | 6/1981 | Fischer | |
| 4,361,648 A | 11/1982 | Shuenn-Tzong | |
| 5,362,650 A * | 11/1994 | Harp | G01N 31/22 436/125 |
| 5,491,094 A * | 2/1996 | Ramana | G01N 31/22 422/420 |
| 6,004,820 A | 12/1999 | Brayton | |
| 6,030,842 A | 2/2000 | Peachey-Stoner | |
| 6,087,089 A | 7/2000 | Wu | |

(Continued)

FOREIGN PATENT DOCUMENTS

WO    WO02/39081    *    5/2002

OTHER PUBLICATIONS

WO2015023362 (PCT/US14/43419); International Search Report and Written Opinion; 8 pages; Oct. 10, 2014.

*Primary Examiner* — Lore Jarrett
(74) *Attorney, Agent, or Firm* — Robert L. Wolter; Beusse, Wolter, Sanks & Maire, PLLC

(57) ABSTRACT

A test element (10) used to determine concentration levels of free and total chlorine in a water sample comprises a test pad (12) adhered to a substrate (14), wherein the test pad (12) is impregnated with a stabilized DPD solution. The test pad (12) is color responsive to different concentration levels of chlorine in the water and compared to a color chart to determine the level of free chlorine and/or total chlorine in the water. The stabilized DPD solution may include N,N-diethyl-p-phenylenediamine oxalate salt, a polymeric anhydride such as a methyl-vinyl anhydride and an organosulfate such as dimethylsulfone.

12 Claims, 2 Drawing Sheets

(56) References Cited

U.S. PATENT DOCUMENTS

| | | | |
|---|---|---|---|
| 6,180,412 B1 * | 1/2001 | Kroll | G01N 33/182 |
| | | | 422/408 |
| 6,432,717 B1 | 8/2002 | Fernando | |
| 7,333,194 B2 | 2/2008 | Jaunakais et al. | |
| 7,491,546 B2 | 2/2009 | Jaunakais | |
| 2006/0073603 A1 | 4/2006 | Jaunakais | |

* cited by examiner

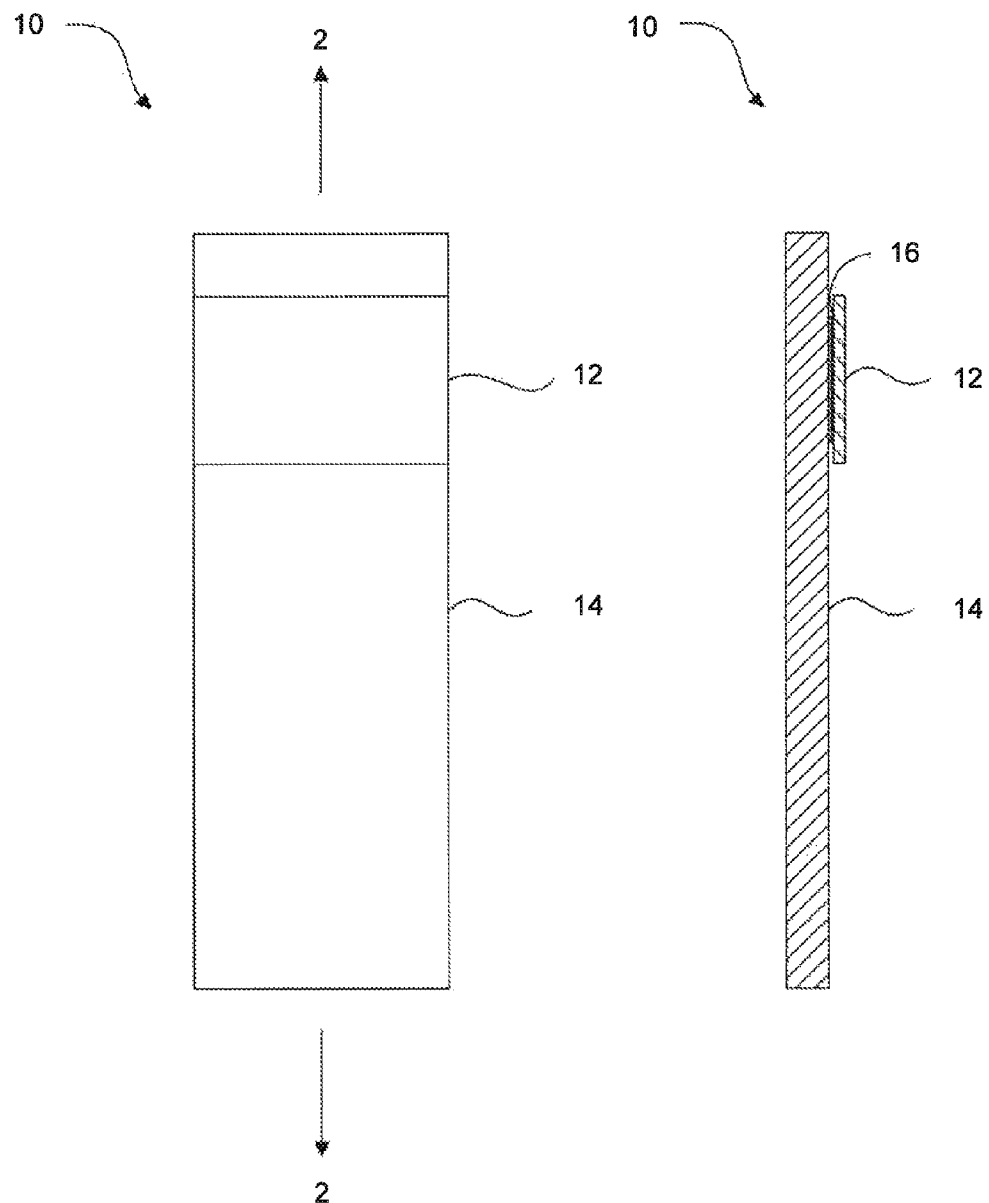

CHLORINE ANALYTICAL TEST ELEMENT AND A STABILIZED N, N-DIETHYL-P-PHENYLENEDIAMINE SOLUTION

CROSS-REFERENCE TO RELATED APPLICATIONS

This application claims the benefit of U.S. Provisional Application No. 61/866,738 filed Aug. 16, 2013, and incorporated herein by reference in its entirety.

BACKGROUND OF THE INVENTION

The DPD (N,N-diethyl-p-phenylenediamine) method for testing chlorine levels was introduced in 1957, and has become the most widely used method for determining free and total chlorine in water. The test has always been used as a liquid test and not developed as a reagent strip for dipping and reading the color by comparing it to a color chart. Current tests in the market that are called DPD strip tests are merely transfer tests not for dip-and-read.

Two standard DPD colorimetric methods are generally recognized in the international community and approved by most states for testing pools and spas. DPD test methods are based on liquid test kits that involve mixing a sample of pool water with chemicals dispensed from a dropper bottle and reading the color developed with a photometer. Those that are currently called DPD test strips have DPD powder attached to a paper or plastic strip/stick. The strip is dipped in a tube of water collected from a pool or spa allowing the powder to dissolve in the water sample and react with any chlorine to give a pink color. The developed color is then read by comparison to a color chart, or on a colorimeter or photometer type device. In essence, the strip-type device is merely a transfer agent for the DPD powder. Each of the U.S. Pat. Nos. 7,491,546; 7,333,194; and, 6,004,820 disclose delivery-type devices, not dip-and-read test strips.

Some prior art (U.S. Pat. Nos. 3,937,613 and 4,275,031) describe reagent delivery devices that include inert plastic strips that are rigid enough to release the reagents by stirring the stick and reading the pink color with a photometer. In U.S. Pat. No. 4,275,031, Fisher et al. describe the use of polyvinyl alcohol (PVA) as an embedding polymer for DPD sulfate and waiting for ten minutes instead of immediate reading. Supposedly, the PVA dissolves in the sample and releases the DPD sulfate suggesting the PVA is an embedding polymer that retards the release of the DPD sulfate. Again, the color developed is read by use of a hand-held color reading device. The transfer agent can be of variable thickness or texture, but it must be able to deliver enough analytical reagent for immediate photometric analysis of free chlorine with accuracy. What is needed is a more stable formulation of DPD for use on test strips.

SUMMARY OF THE INVENTION

An embodiment of the invention includes a test element for detecting concentration levels of chlorine in water. More specifically, the test element comprises a substrate for securing a test pad to and being adapted for human handling. A test pad is secured to the substrate and is impregnated with a dried solution comprising a phenylenediamine salt, an oxidation inhibitor and an organo-sulfur compound. When wetted with a water sample, the test pad is color responsive to chlorine species in the water sample indicative of concentration levels of free and/or total chlorine in the water.

In another embodiment, the invention also includes a composition of matter comprising a phenylenediamine salt, an oxidation inhibitor and an organo-sulfur compound.

In yet another embodiment, the subject invention may also include a kit for detecting concentration levels of chlorine in water. The kit may comprise a test element including a substrate and a test pad on the substrate that is impregnated with a dried solution comprising a phenylenediamine salt, an oxidation inhibitor and an organo-sulfur compound. When wet, the test pad is color responsive to chlorine species in water indicative of concentration levels of free and/or total chlorine in the water. The kit may also comprise a color chart including a plurality of different colored areas, wherein each colored area represents a different concentration level of chlorine in water.

In any of the above described embodiments of the invention, the phenylenediamine salt may be N,N-diethyl-p-phenylenediamine oxalate; and, the oxidation inhibitor may comprise at least one polymeric anhydride. The polymeric anhydride may be a methylvinylether anhydride polymer, and/or the polymeric anhydride may be methylvinylether-maleic anhydride copolymer. The organo-sulfur compound may be dimethylsulfone.

An embodiment of the invention may also encompass a test element with a test pad that is subjected to an impregnation process. The test element for detecting concentration levels of chlorine in water comprises a substrate for securing a test pad to and being adapted for human handling. The impregnation process comprises contacting the test pad matrix material with a first solution comprising an oxidation inhibitor. In an embodiment the first solution 0.1% $Na_2EDTA$, 0.1% sodium lauryl sulfate, and 0.1% MES buffer pH adjusted to about 6.4, and then adding 5.0% aqueous solution of Gantrez AN-119 (oxidation inhibitor) in a ratio of MES:Na2EDTA:SDS:Gantrez of 0.3:0.04:0.04 1. The test pad matrix material is then dried. The process further comprises contacting the dried test pad matrix material with a second solution comprising an oxidation inhibitor, a phenylenediamine salt and an organo-sulfur compound. In an embodiment the second solution may comprise 1.0% Gantrez AN-119 containing 5% ethanol, 0.145 g DPD oxalate salt and 0.1 g of dimethylsulfone. The test pad matrix material is then dried for a second time. Known assembly processes may be used to affix the test pad matrix material to a substrate material and then separate the combined components into test elements include a test pad affixed to a substrate. When the test pad is wetted with a water sample, the test pad is color responsive to chlorine species in the water sample indicative of concentration levels of free and/or total chlorine in the water.

BRIEF DESCRIPTION OF THE DRAWINGS

A more particular description of the invention will be rendered by reference to specific embodiments thereof that are illustrated in the appended drawings. Understanding that these drawings depict only typical embodiments of the invention and are not therefore to be considered to be limiting of its scope, the embodiments of the invention will be described and explained with additional specificity and detail through the use of the accompanying drawings in which:

FIG. 1 is a front view of a test element in accordance with an embodiment of the invention.

FIG. 2 is a cross-sectional view of the test element of FIG. 1.

DETAILED DESCRIPTION OF THE INVENTION

Figure 3:
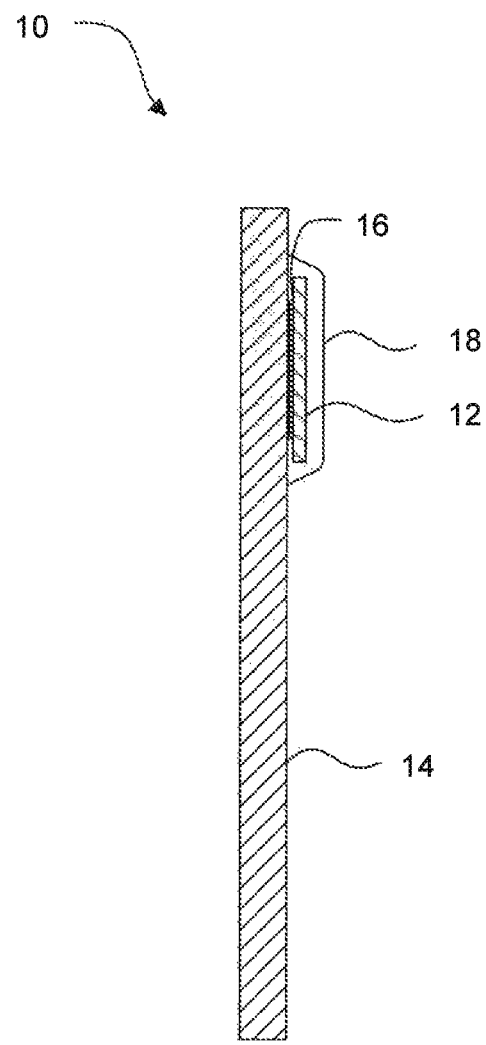
FIG. 3 is a cross-sectional view of the test element of FIG. 2 with the added construction of a water-permeable overlay affixed over the pad.

A more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained.

With respect to FIG. 1, a reagent test element 10 is shown and is preferably used to test for chlorine levels in a chlorinated water source such as a pool or spa utilizing DPD (N, N-diethyl-p-phenylenediamine), and/or a DPD salt, as a coloring indicator or reagent. For example, the test element 10 may be color responsive to different concentration levels of 0, 1, 3, 5 and 10 ppm free chlorine in water. In an embodiment of the invention, the test element 10 includes a water adsorbent test pad 12 or similar hydrophilic material affixed to a substrate 14, and the pad 12 is impregnated with a solution including DPD, a polymeric stabilizer, and binders. The test element 10 may be used in conjunction with a color chart including a plurality of different colored areas, wherein each colored area represents a different concentration level of chlorine in water. While the test element 10 shown in FIG. 1 includes a single test pad 12, the test element 10 may have a plurality of test pads wherein each test pad impregnated with one or more reagents to test for different characteristics of a fluid sample.

Typical matrix materials for a test pad may comprise absorbent paper, both natural and synthetic, as well as woven and non-woven, and porous or nonporous polymeric materials whereby the test composition is mixed with the matrix material prior to its being dried or solidified. The matrix must however be impervious to and not react with the fluid being tested and must be reasonably hydrophilic and porous so that the fluid being tested wets the matrix and the analyte or reagent contained therein reacts with the incorporated reagent composition. Other test elements may be prepared by attaching the test composition onto the surface of the carrier by chemical or physical methods. Depending on the test element design and use, the matrix structure may be flat or curved and the surface thereof may be smooth or rough.

An example of a polymeric stabilizer used herein (also referred to as an oxidation inhibitor) is from the generic class of polymeric anhydrides such as Gantrez® AN-119 sold by Ashland, Inc. Gantrez AN-119 is a co-polymer of maleic anhydride and methylvinylether. It is also generically called a methylvinylether anhydride. Other polymers from the class of polymeric anhydrides could also presumably be used to similar effect, and the teachings herein may be thus extended. In addition, the solution may include an organo-sulfur compound including dimethylsulfone, also referred to as methylsulfonylmethane (MSM). The test pad 12 is attached to the substrate 14 using any suitable adhesive 16 known to those skilled in the art.

The test pad 12 was impregnated with the stabilized DPD reagent in a two-step process, that included: 1) first dipping the test pad in an aqueous solution containing the polymeric stabilizer, then drying the test pad; and, 2) dipping the test pad in a second aqueous solution containing the polymeric stabilizer/binder, DPI) and organo-sulfur compound. The test pad was then dried according to a predetermined heating schedule.

When the test element 10, including the test pad 12, was dipped into a water sample containing chlorine, the test pad 12 developed a color on the pad, which was indicative of a concentration of chlorine in the water sample, which may be free chlorine or total chlorine. In a non-limiting example, the test pad 12 color turns various shades of red and can be compared to a color chart to determine an amount of free chlorine present in the water sample. The reacted materials remain on the pad due to the binding action of the polymers.

In an alternative embodiment, an overlay of a water-permeable material may aid in retention of the chemicals within the pad. The FIG. 3 shows a cross-section of the test element 10 having a water-permeable membrane 18 of a flexible polymer affixed over the surface of the test pad 12, but leaving the edges of the test pad 12 open. The flexible polymer membrane 18 affords some mechanical stability to the test pad 12, and also retains any DPD or associated chemicals that may be dissociated from the test pad 12 during shipment. The water permeable membrane 18 may also serve to aid in containing chemicals and prevent wash-out of the chemical reagents during testing. In addition, the membrane 18 may also ensure an even appearance in coloration as a result of the chemical containment.

With respect to the above-described impregnating process, non-limiting examples of test solutions and test results are provided below. Unless otherwise indicated, all general reagents were Reagent Grade or better, and were obtained from a general source such as Fischer Scientific.

First Solution 20 mL of a solution of 0.1 M MES (N-(4-Morpholino) ethane sulfonic acid) buffer comprising 0.1% $Na_2EDTA$ and 0.1% Sodium lauryl sulfate (SDS) was adjusted to about pH 6.40, with 1N NaOH. To this solution was added 10 mL of a Gantrez AN-119 5% (w/w) solution and the volume was brought up to a total of 50 mL with reverse osmosis deionized water (RO/DI). The Gantrez AN-119 solution may be from about 0.5% to about 1.25% Gantrez. Preferably the solution is greater than 1% Gantrez. The reagents in the final solution follow the ratio: MES:Na7EDTA:SDS:Gantrez was 0.3:0.04:0.04:1. The solution was impregnated in Whatman 740E filter paper and dried for 15 minutes at 100 degrees C., in an air/flow type oven suitable for maintaining the temperature and drying the paper. The pH of the solution should be adjusted to be preferably less than 6.4, more preferably from 5.85 to 6.4, and most preferred is 5 to 5.85.

Second Solution

To a second aqueous solution of 1.0% Gantrez AN-119 containing 5% ethanol was added 0.145 g of DPD oxalate salt and 0.1 g of dimethylsulfone. The currently preferred pH range is less than pH 5, a more preferred range is between 2 and 5, and a most preferred pH range is from about pH 3 to about pH 4. This solution was mixed until dissolved at room temperature. The dried paper impregnated from the first solution was dipped in this solution and again dried in the oven at 100 degrees C. for 15 minutes. The ethanol may be from about 5% to about 10% ethanol, and other alcohols such as reagent alcohol and isopropyl alcohol may be used. The paper was then attached to a double-sided adhesive paper and attached to a plastic sheet (polystyrene), which was cut into individual test strips measuring approximately 3.25 inches by 0.20 inches. The test strips were tested by dipping them into different chlorine-water solutions and immediately comparing the colors to a color chart. The reagent was able to distinguish between 0, 1, 3, 5 and 10 ppm chlorine in water, according to the test results shown in the table below.

Test Results

The reagent was fast in giving results and can distinguish levels of 0, 1, 3, 5 and 10 ppm free chlorine. As a measure of color progression, a color spectrophotometer was used to demonstrate the reacted color for each tested Free Chlorine sample. The colors are depicted by Lab color space including a color-opponent space with dimension "L" for lightness and "a" and "b" for the color-opponent dimensions, based on nonlinearly compressed CIE XYZ color space coordinates. Unlike the RGB and CMYK color models, Lab color is designed to approximate human vision. When the reacted test strip was measured using an X-rite brand of color reflectance spectrodensitometer capable of measuring the color coordinates of each resulting color, the following results were obtained. An additional column in the data table provides the customary color that would typically describe the reacted color.

| Test Sample | Color Coordinates Measured | | | Visual Description |
|---|---|---|---|---|
| Free Chlorine (ppm) | L* | a* | b* | Visual Color |
| 0 | 69.29 | 1.99 | 3.61 | Off-white |
| 1 | 69.79 | 5.29 | 3.13 | Light pink |
| 3 | 64.16 | 10.72 | 3.31 | pink |
| 5 | 62.40 | 12.19 | 3.10 | Dark pink |
| 10 | 56.35 | 28.57 | −0.34 | Magenta |

The three parameters L*, a* and b* correlate to the X-rite instruments read-outs lightness, color and saturation, respectively. Parameter a*, color, is most closely correlated to the free Chlorine ppm levels. It can be seen that as the color develops from a faint pink (1 ppm) to a red (10 ppm) the a* values increase from approximately 2 to 28.57.

The Test Pad Impregnation and Test Element Assembly Process

An embodiment of the invention may also encompass a test element with a test pad that is subjected to an impregnation process. The test element for detecting concentration levels of chlorine in water comprises a substrate for securing a test pad to and being adapted for human handling. A test pad is secured to the substrate and is impregnated with a solution comprising a phenylenediamine salt, an oxidation inhibitor and an organo-sulfur compound and dried. The impregnation process comprises:

1) Contacting a test pad matrix material with a first solution comprising at least an oxidation inhibitor. In an embodiment the firs solution may comprise 0.1% Na₂EDTA, 0.1% sodium lauryl sulfate, and 0.1 MES buffer pH adjusted to about 6.4, and then adding 5.0% aqueous solution of Gantrez AN-119 in a ratio of MES:Na2EDTA:SDS:Gantrez of 0.3:0.04:0.04 1; and, 2) then drying the test pad matrix material.

3) The process further comprises contacting the dried test pad with a second solution comprising a diphenylenediamine salt, an oxidation inhibitor and an organo-sulfure compound. In an embodiment the second solution comprises 1.0% Gantrez AN-119 containing 5% ethanol, 0.145 g DPD oxalate salt and 0.1 g of Dimethyl sulfone; and, 4) then drying the test pad for a second time.

A test pad impregnated according to the above-describe process, when wetted with a water sample, is color responsive to chlorine species in the water sample indicative of concentration levels of free and/or total chlorine in the water.

Test elements and test pads are then assembled by affixing the test pad matrix material to a substrate material using any adhesive known to those skilled in the art. In an embodiment a water permeable membrane is affixed to the substrate material covering the now impregnated matrix material. The substrate material with the attached impregnated test pad matrix material is then separated into a plurality of test elements, wherein each test element has at least one test pad impregnated with the dried reagent solutions. By way of example, the substrate material with the impregnated material may be cut into 0.2 inches wide by 3.25 inches long strips.

DPD solutions are notoriously unstable when exposed to UV light, temperature, heavy metals or moisture for any extended period of time. Most DPD applications are handled in temperature and humidity controlled conditions to prevent the DPD indicator from oxidation by atmospheric oxygen or other potential interferents. By way of example, DPD and other reagents are typically stored in glass ampoules under vacuum to prevent premature reactivity until ready for use, when the ampoule tip is broken off. This could result in injury if contact is made with the broken ampoule tip.

The inventors have discovered that by adding dimethylsulfone to the DPD and Gantrez AN-119 co-polymer mix, at a controlled system pH, the test pad 12 is reactive even after four weeks of storage at 50 degrees C. in the oven. Without the dimethylsulfone, the strips were mottled in color or window framed (dark edges, light center). The use of polyvinylalcohol (PVA), polyvinylpyrollidone (PVP) or hydroxymethylcellulose polymers did not provide a stable strip even at room temperature. Only the combination of Gantrez AN-119 and dimethylsulfone provided the stability expected of this product.

The predominant reaction of DPD in water in the presence of free chlorine is as follows:

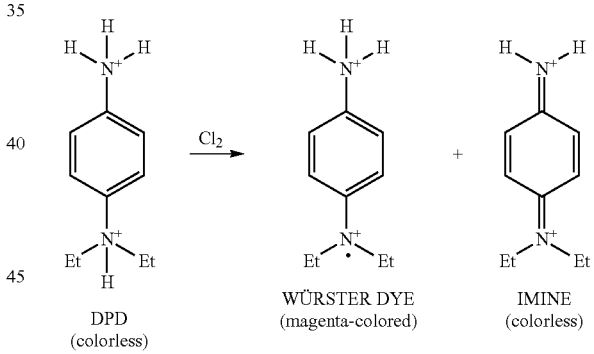

The imine product is favored when high levels of chlorine are present, and this is why most DPD methods are only accurate below a certain level of chlorine. The invention disclosed herein has been demonstrated to be reactive up to 50 ppm Free Chlorine.

It is well-known in the art that Gantrez AN-119 hydrolyzes forming carboxylic groups that inhibit the nitrogen of the DPD from prematurely oxidizing. EDTA (Na₂EDTA) is a well-known metal ion chelator, and it will undergo a reaction with free metal ions wherein the Na₂EDTA will form a coordination complex with metal ions such as manganese and iron (ferric and ferrous). Without Na₂ETDA in the formulation, these oxidizing metals can interfere with DPD to generate the oxidized Wurster dye, which would be a "false positive" in terms of the chlorine test.

In alternate embodiments, the combination of constituent compounds or similar compounds may be used to stabilize DPD distributed in forms other than on a test pad of a test strip. For example, the above-described stabilized DPD solution may take the form of a powder or a tablet form that imparts more stability, expanded range of testing, and longer shelf life.

Solutions prepared as described with dimethylsulfone added were found to be stable for three days in a beaker on the lab bench. The same solution stored in the refrigerator was found to be colorless after two weeks with no sign of autoxidation or premature reactivity. This will make it easy to manufacture the product because of the long shelf-life of the solution.

The reagent test strips were also found to be very stable. Incubation in an oven at 50 degrees C. for almost four weeks did not show extensive loss of reactivity. Color fading was observed at the low levels, but there was still enough color development to detect the presence of chlorine. This was surprising given that DPD will normally readily oxidize under these same conditions.

In most of the prior art as described in the above-listed patents, emphasis was placed on the separation of the DPD from the phosphate buffer until time of application, to prevent instability and inaccurate results because of premature reactivity. Embodiments of the above-described invention have a test pad impregnated with a stabilized DPD solution, whereby the reaction between the DPD and chlorine occurs on the wetted test pad, which provides a color indication of concentration levels of chlorine in water. The prior art describes test strips that are transfer or dosing agents. No hand-held device is required to read the test element of the subject invention. No mixing of different liquids is required, and it is convenient and user friendly.

This written description uses examples to disclose embodiments of the invention to enable any person skilled in the art to make and use the embodiments of the invention. The patentable scope of the embodiments of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A test element for detecting concentration levels of chlorine in water comprising:

a substrate for securing a test pad to and being adapted for human handling;

a test pad secured to the substrate that is impregnated with a dried solution comprising a phenylenediamine salt, an oxidation inhibitor and an organo-sulfur compound, wherein the organo-sulfur compound comprises dimethylsulfone; and wherein when wetted with a water sample, the test pad is color responsive to chlorine species in said water sample indicative of concentration levels of free and/or total chlorine in the water.

2. The test element of claim 1, wherein the phenylenediamine salt is N,N-diethyl-p-phenylenediamine oxalate.

3. The test element of claim 1, wherein the oxidation inhibitor comprises at least one polymeric anhydride.

4. The test element of claim 3, wherein the at least one polymeric anhydride is a methylvinylether anhydride polymer.

5. The test element of claim 3, wherein said at least one polymeric anhydride is methylvinylyether-maleic anhydride copolymer.

6. The test element of claim 1 further comprising a water permeable membrane attached to the substrate covering the test pad.

7. The test element of claim 1 wherein the test element is used in connection with a color chart including a plurality of different colored areas, wherein each colored area represents a different concentration level of chlorine in water.

8. A composition of matter comprising a phenylenediamine salt, an oxidation inhibitor and an organo-sulfur compound, wherein the organo-sulfur compound comprises dimethylsulfone.

9. The composition of claim 8, wherein the phenylenediamine salt is N,N-diethyl-p-phenylenediamine oxalate.

10. The composition of claim 8, wherein the oxidation inhibitor comprises at least one polymeric anhydride.

11. The composition of claim 10, wherein the at least one polymeric anhydride is a methylvinylether anhydride polymer.

12. The composition of claim 10, wherein the at least one polymeric anhydride is methylvinylyether-maleic anhydride copolymer.

* * * * *